United States Patent
Fukuda

(10) Patent No.: US 8,187,454 B2
(45) Date of Patent: May 29, 2012

(54) DEGRADATION DETECTOR AND DETECTING METHOD

(75) Inventor: Haruki Fukuda, Nishikamo-gun (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 715 days.

(21) Appl. No.: 11/792,527

(22) PCT Filed: Dec. 14, 2005

(86) PCT No.: PCT/JP2005/023432
§ 371 (c)(1), (2), (4) Date: Jun. 7, 2007

(87) PCT Pub. No.: WO2006/077711
PCT Pub. Date: Jul. 27, 2006

(65) Prior Publication Data
US 2008/0128277 A1      Jun. 5, 2008

(30) Foreign Application Priority Data

Jan. 19, 2005   (JP) .................... 2005-011572

(51) Int. Cl.
*G01N 27/41* (2006.01)
*G01N 27/407* (2006.01)

(52) U.S. Cl. ....... 205/785; 205/775; 205/784; 73/23.31; 73/23.32; 701/109; 123/697; 123/690; 204/408; 204/424; 204/401; 204/406

(58) Field of Classification Search .......... 204/401, 204/421–429; 205/775, 784.5, 784, 785; 219/202–208, 482–506; 73/23.31, 23.32; 123/690, 697; 701/109
See application file for complete search history.

(56) References Cited

U.S. PATENT DOCUMENTS

| | | | | |
|---|---|---|---|---|
| 4,708,777 A * | 11/1987 | Kuraoka | ............ | 205/784.5 |
| 5,020,499 A * | 6/1991 | Kojima et al. | ........... | 123/479 |
| 5,263,358 A * | 11/1993 | Center et al. | ........... | 73/23.32 |
| 5,709,198 A | 1/1998 | Sagisaka et al. | | |
| 6,258,232 B1 * | 7/2001 | Hasegawa et al. | ........... | 204/424 |
| 2002/0060150 A1 * | 5/2002 | Hashimoto et al. | .......... | 204/401 |
| 2004/0099528 A1 * | 5/2004 | Hattori | ........... | 204/401 |
| 2005/0010323 A1 * | 1/2005 | Cocciadiferro et al. | ....... | 700/174 |

FOREIGN PATENT DOCUMENTS

| | | |
|---|---|---|
| JP | A 2002-155796 | 5/2002 |
| JP | A 2003-50227 | 2/2003 |

* cited by examiner

*Primary Examiner* — Jeffrey T Barton
*Assistant Examiner* — Jennifer Dieterle
(74) *Attorney, Agent, or Firm* — Oliff & Berridge, PLC

(57) ABSTRACT

A degradation detector of an exhaust gas sensor is disclosed. The detector comprises a first heater resistance estimator (16) for estimating a resistance of a heater that heats the exhaust gas sensor, based on a device resistance of the exhaust gas sensor; a heater resistance calculator (17) for calculating a resistance of the heater, based on a heater current of the heater; and a degradation determiner (18) for determining whether the exhaust gas sensor is degraded, by comparing the estimated resistance of the heater and the calculated resistance of the heater.

6 Claims, 8 Drawing Sheets

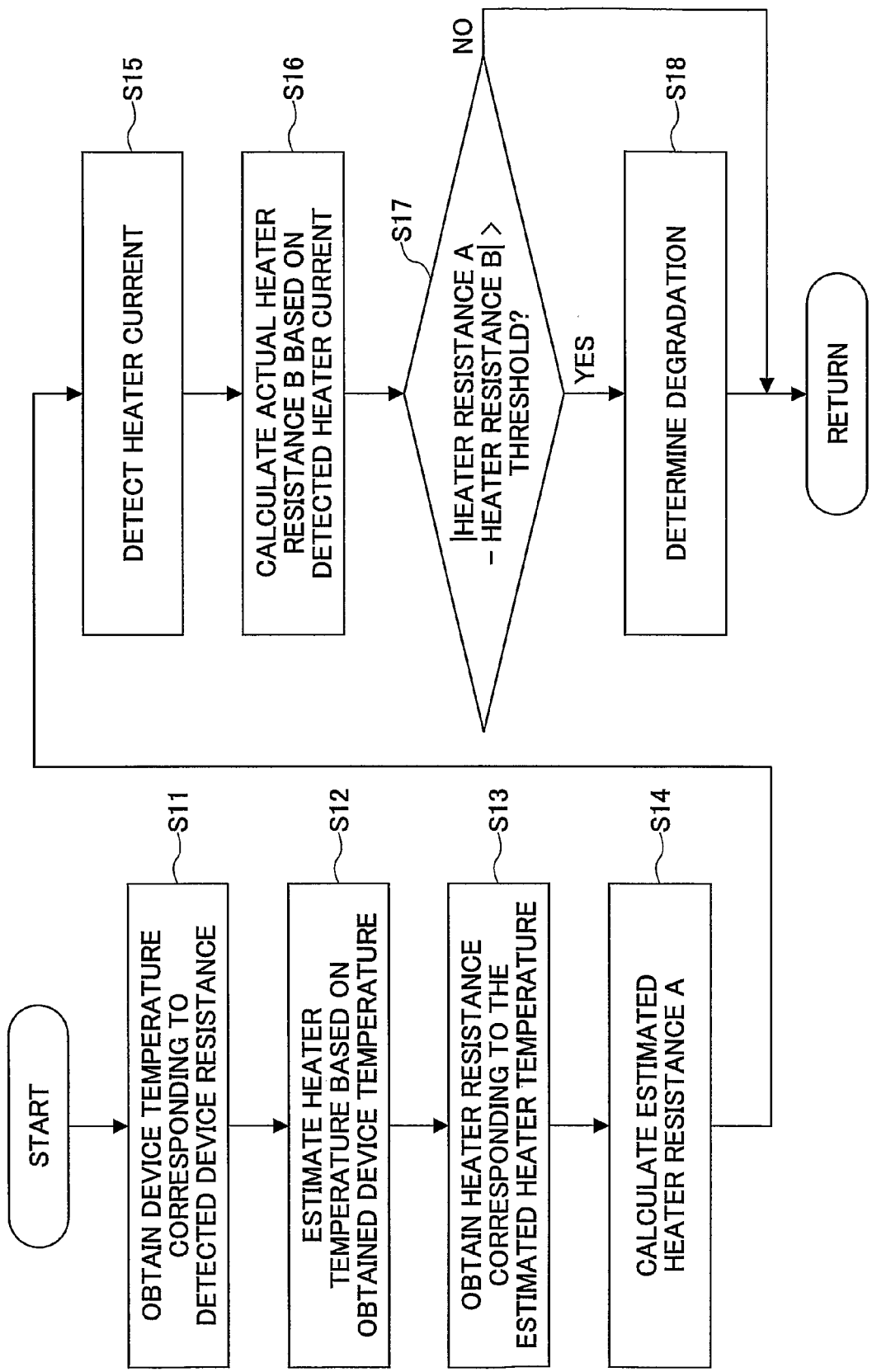

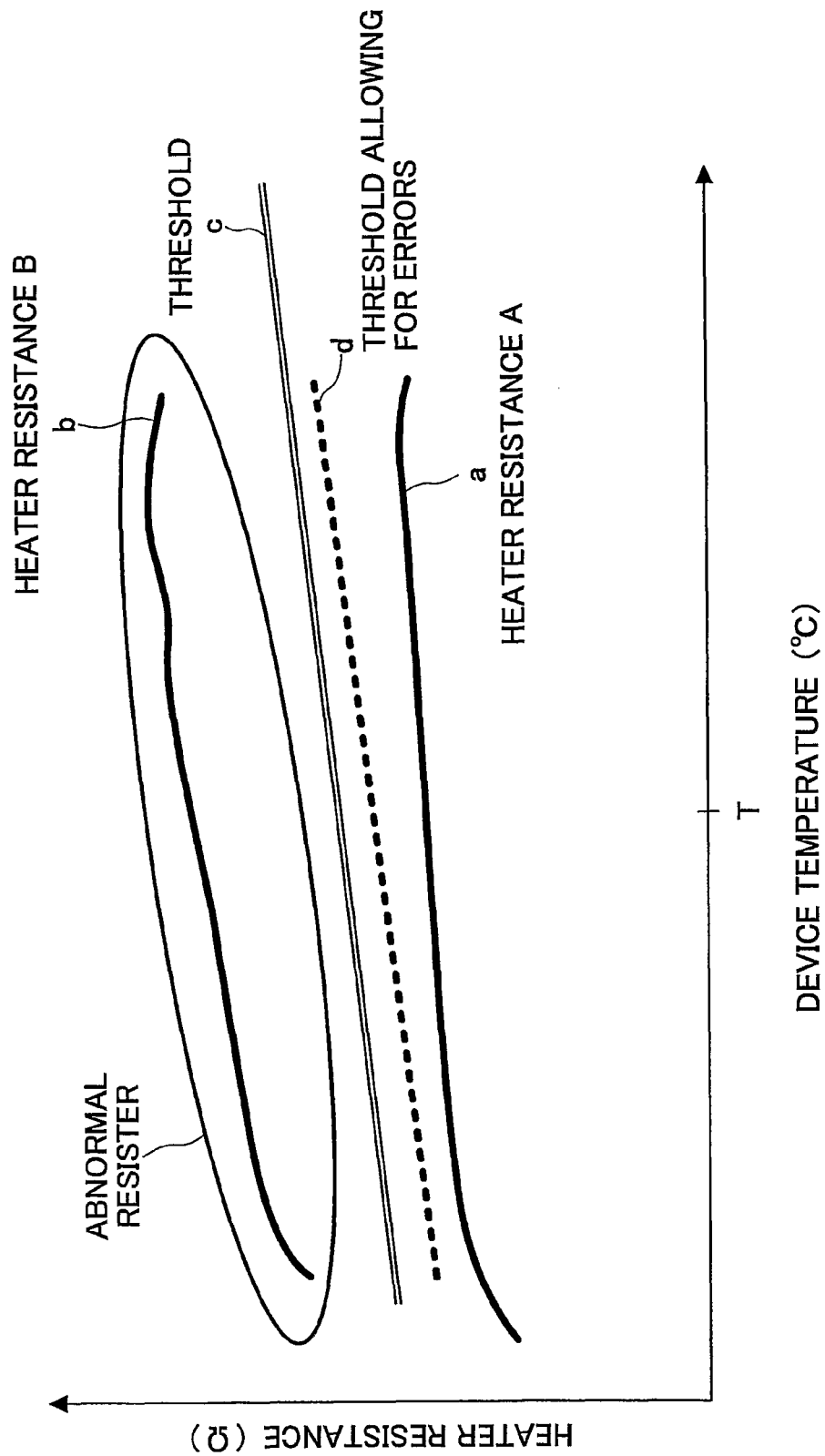

DEGRADATION DETECTOR AND DETECTING METHOD

TECHNICAL FIELD

The present invention generally relates to a degradation detector and a degradation detecting method in a vehicle exhaust gas sensor.

BACKGROUND ART

It is regulated that exhaust gas emitted from internal-combustion engines of automobiles contains $NO_X$, etc. (referred to as "specific gas" herein) concentration less than a defined amount. Therefore, the exhaust gas is monitored by a gas concentration sensor mounted on the automobile. The gas concentration sensor is provided in a solid electrolyte device. The solid electrolyte device is heated by heaters so that its temperature is raised to an active temperature of the specific gas. If the heater performance is degraded and the solid electrolyte is not heated enough or is overheated, the specific gas cannot be maintained at the active state to make it difficult to precisely detect the specific gas.

Therefore, it is desired to detect the degradation of the heater performance. As such detectors, a scheme is proposed where the initial state and the present state of the heaters are compared to detect the degradation of the heater performance, as disclosed in Japanese Patent Laid-open Publication No. 2002-155796. In this scheme, the initial states and the present states of the gas concentration sensor and the heaters are compared. If they are significantly changed, it is determined that the performance of the heaters is degraded.

This scheme, however, monitors the internal resistances of the actually used gas concentration sensor and heaters as their present internal resistances. The internal resistances of the actually used gas concentration sensor and heaters can be significantly changed, and therefore the present internal resistances cannot be reflected or detected and the correct comparison with the initial internal resistance of the heaters are not achieved.

DISCLOSURE OF THE INVENTION

It is a general object of the present invention to provide a degradation detector and detecting method in an exhaust gas sensor, which can accurately detect the degradation of the exhaust sensor.

Features and advantages of the present invention are set forth in the description that follows, and in part will become apparent from the description and the accompanying drawings, or may be learned by practice of the invention according to the teachings provided in the description. Objects as well as other features and advantages of the present invention will be realized and attained by an information recording apparatus and a method thereof particularly pointed out in the specification in such full, clear, concise, and exact terms as to enable a person having ordinary skill in the art to practice the invention.

To achieve these and other advantages and in accordance with the purpose of the invention, as embodied and broadly described herein, the invention provides as follows.

According to one aspect of the present invention, a degradation detector of an exhaust gas sensor comprises:

a first heater resistance estimator for estimating a resistance of a heater that heats the exhaust gas sensor, based on a device resistance of the exhaust gas sensor;

a heater resistance calculator for calculating a resistance of the heater, based on a heater current of the heater; and a degradation determiner for determining whether the exhaust gas sensor is degraded, by comparing the estimated resistance of the heater and the calculated resistance of the heater.

According to other aspect of the present invention. The degradation detector further comprises:

a device temperature-device resistance map for storing a relationship between the device resistances and temperatures of the device; and a heater temperature-heater resistance map for storing a relationship between temperatures of the heater and the heater resistances;

wherein the first heater resistance estimator obtains a device temperature from the device temperature-device resistance map, based on the device resistance of the exhaust gas sensor;

estimates a temperature of the heater, based on the obtained device temperature, and obtains a heater resistance from the heater temperature-heater resistance map, based on the estimated heater temperature.

According to other aspect of the present invention, a degradation detector of a vehicle exhaust gas sensor comprises:

a second heater resistance estimator for estimating a resistance of a heater that heats the exhaust gas sensor, based on one or more temperatures detected by temperature sensors provided at places of the vehicle;

a heater resistance calculator for calculating a resistance of the heater, based on a heater current of the heater; and a degradation determiner for determining whether the exhaust gas sensor is degraded, by comparing the estimated resistance of the heater and the calculated resistance of the heater.

According to other aspect of the present invention, the degradation detector further comprises:

a heater temperature-heater resistance map for storing a relationship between temperatures of the heater and the heater resistances;

wherein the second heater resistance estimator estimates the heater temperature when a soak time exceeded a predetermined value, based on the one or more temperatures detected by the temperatures sensors; and obtains a heater temperature from the heater temperature-heater resistance map, based on the estimated heater resistance.

According to other aspect of the present invention, in the degradation detector the second heater resistance estimator estimates the heater temperature, based on one or more of an intake air temperature, an A/F sensor heater temperature, a sub O2 sensor heater temperature, an atmospheric temperature or an engine cooling water temperature.

According to other aspect of the present invention, a degradation detecting method in an exhaust gas sensor comprises the steps of:

estimating a resistance of a heater that heats the exhaust gas sensor, based on a device resistance of the exhaust gas sensor;

calculating a resistance of the heater, based on a heater current of the heater; and determining whether the exhaust gas sensor is degraded, by comparing the estimated resistance of the heater and the calculated resistance of the heater.

According to other aspect of the present invention, the degradation detecting method further comprises the steps of:

preparing a device temperature-device resistance map for storing a relationship between the device resistances and temperatures of the device; and preparing a heater temperature-heater resistance map for storing a relationship between temperatures of the heater and the heater resistances;

wherein the step of estimating a resistance of a heater includes the steps of:

obtaining a device temperature from the device temperature-device resistance map, based on the device resistance of the exhaust gas sensor;

estimating a temperature of the heater, based on the obtained device temperature, and obtaining a heater resistance from the heater temperature-heater resistance map, based on the estimated heater temperature.

According to other aspect of the present invention, a degradation detecting method in a vehicle exhaust gas sensor comprises the steps of:

estimating a resistance of a heater that heats the exhaust gas sensor, based on one or more temperatures detected by temperature sensors provided at places of the vehicle;

calculating a resistance of the heater, based on a heater current of the heater; and determining whether the exhaust gas sensor is degraded, by comparing the estimated resistance of the heater and the calculated resistance of the heater.

According to other aspect of the present invention, the degradation detecting method further comprises the step of:

preparing a heater temperature-heater resistance map for storing a relationship between temperatures of the heater and the heater resistances;

wherein the step of estimating a resistance of a heater includes the steps of:

estimating the heater temperature when a soak time exceeded a predetermined value, based on the one or more temperatures detected by the temperatures sensors; and obtaining a heater temperature from the heater temperature-heater resistance map, based on the estimated heater resistance.

According to other aspect of the present invention, in the degradation detecting method the step of estimating a resistance of a heater includes a step of estimating the heater temperature, based on one or more of an intake air temperature, an A/F sensor heater temperature, a sub O2 sensor heater temperature, an atmospheric temperature or an engine cooling water temperature.

BRIEF DESCRIPTION OF THE DRAWINGS

FIG. 4 is a flowchart illustrating a procedure for detecting the degradation of an exhaust gas sensor.

FIG. 5 is a graph showing the relationships between heater temperatures and heater resistance.

BEST MODE FOR CARRYING OUT THE INVENTION

In the following, best mode embodiments of the present invention are described with reference to the accompanying drawings.

Degradation detectors for an exhaust gas sensor according to the embodiments of the present invention are explained with reference to FIG. 1 through FIG. 9. The degradation detector for an exhaust gas sensor detects the performance degradation of a heater in the exhaust gas sensor, based on the electrical resistance of the heater.

Figure 1:
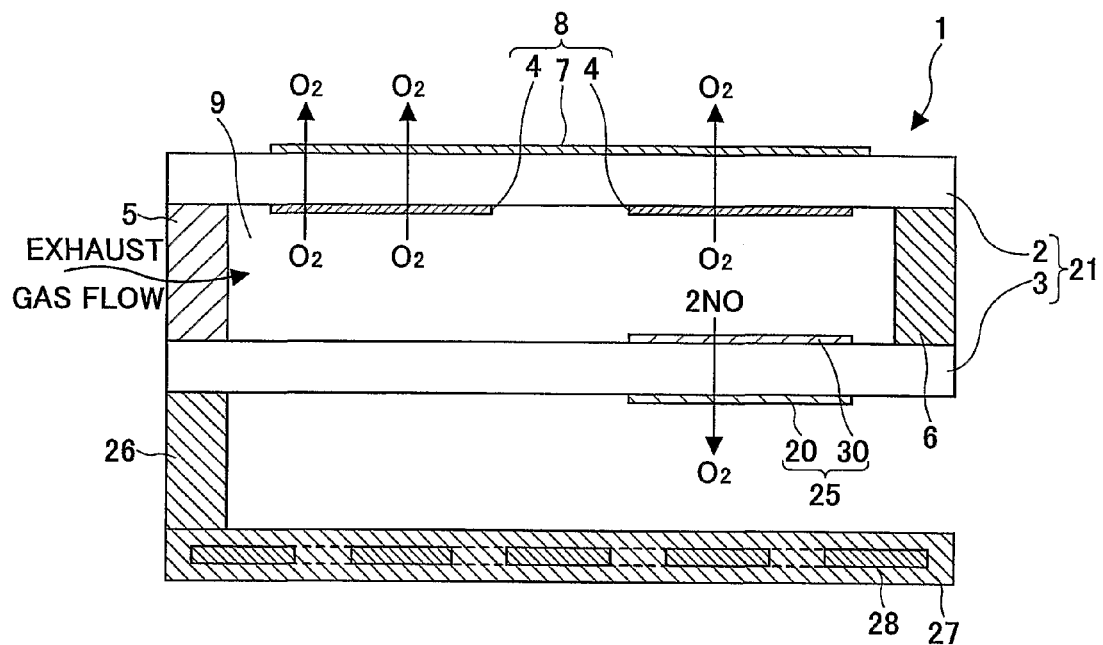
FIG. 1 is a schematic view of an exhaust gas sensor.

An exhaust gas sensor is briefly explained. FIG. 1 shows a schematic diagram of a typical exhaust gas sensor 1. The exhaust gas sensor 1 comprises an exhaust gas chamber 9 defined between a pair of bulkheads 2, 3 including solid electrolyte. Exhaust gas is introduced into the exhaust gas chamber 9. The exhaust gas sensor 1 further comprises oxygen pump electrodes 8 and $NO_X$ detection electrodes 25. The oxygen pump electrodes 8 are positioned on both surfaces of the bulkhead 2 and discharge oxygen ions from the exhaust gas chamber 9 to the outside as shown in FIG. 1 by applying electric voltage. The $NO_X$ detection electrodes 25 are positioned on both surfaces of the bulkhead 3, decompose $NO_X$ within the exhaust gas chamber 9 and discharge generated oxygen ions to the outside of the exhaust gas chamber. The $NO_X$ detection electrodes 25 measure $NO_X$ concentration within the exhaust gas chamber based on an electric current amount generated when discharging the oxygen ions.

A heater wall 27 is placed opposing the bulkhead 3 via a spacer 26. The heater wall 27 is made of alumina material. Plural heaters 28 are embedded in the heater wall 27. The heaters 28 are connected to an external power supply (not shown) and heat the exhaust gas sensor 1 to a predetermined temperature.

In the exhaust gas chamber 9, exhaust gas is introduced to an exhaust gas flow path formed between the pair of bulkheads 2, 3. The exhaust gas chamber 9 is defined and separated from the outside by at least the pair of bulkheads 2, 3, a diffusion rate-determining wall 5, and a spacer 6. The diffusion rate-determining wall 5 is made of material which can introduce exhaust gas into the exhaust gas chamber 9 with a predetermined diffusion rate-determining resistance. Such material may be, for example, porous material such as alumina, or porous or non-porous material mixed with microporous material. The spacer 6 is made of normal material such as alumina, etc.

Material having oxygen ion conductivity can be used as the solid electrolyte for the bulkheads 2, 3. Such material may be, for example, normal electrolytes such as zirconia, bismuth oxide, cerium oxide or these materials having yttria, calcia, ceria or magnesia, etc., added.

The oxygen pump electrodes 8 use platinum or a known alloy, etc., having oxygen sensitivity. Electrodes 4 of the oxygen pump electrodes 8 are placed on the chamber side surface of the bulkhead 2. The other electrode 7 is placed on the outer side surface of the bulkhead 2 to form the oxygen pump electrodes 8. By applying a voltage to the oxygen pump electrodes 8, oxygen within the exhaust gas chamber 9 comes into contact with the inner electrodes 4 of the bulkhead 2, is carried to the outer electrode 7 via the solid electrolyte included in the bulkhead 2, and discharged to the outside of the exhaust gas chamber 9. Due to this operation of the oxygen pump electrodes 8, the oxygen partial pressure in the exhaust gas chamber 9 becomes low.

Because of the reduction in the oxygen partial pressure, NO is generated from $NO_X$ within the exhaust gas chamber 9. The generated NO is detected by the $NO_X$ detection electrodes 25. Because of the reduction in the oxygen partial pressure, it becomes unlikely that oxygen included in the exhaust gas will contact the $NO_X$ detection electrodes 25. Accordingly, the $NO_X$ detection electrodes 25 have less measurement error caused by oxygen interference.

The $NO_X$ detection electrodes 25 use, for example, Pt/Rh electrodes, etc., having $NO_X$ selective reducing characteristics. Similar to the oxygen pump electrodes 8, an inner $NO_X$ detection electrode 30 that is one electrode of the $No_X$ detection electrodes 25 is placed on the chamber side of the bulkhead 3, while the other electrode, an outer detection electrode 20, is placed on the outer side of the bulkhead 3 to form the $NO_X$ detection electrodes 25.

When a voltage is applied to the $NO_X$ detection electrodes 25, NO within the exhaust gas chamber is decomposed by the inner $NO_X$ detection electrode 30 due to the above described oxygen pumping operation, to generate oxygen ions. The generated oxygen ions are carried to the outer detection electrode 20 via the solid electrolyte included in the bulkhead 3 and discharged to the outside of the exhaust gas chamber 9. At this time a current is generated, by which $NO_X$ concentration in the chamber is measured. The $NO_X$ detection electrodes 25 are placed at the most downstream side of the exhaust gas flow. The $NO_X$ detection electrodes 25 are placed at the same flow position as the oxygen pump electrodes 8 or more downstream thereof. Not only the $NO_X$ detection electrodes 25, but also several other electrodes for detecting other exhaust gas components can be placed in the exhaust gas chamber.

Embodiment 1

In this embodiment, the electric resistance of the heaters 28 is estimated based on the electric resistance (which may be referred to as just "device resistance" herein) of the solid electrolyte device (solid electrolyte in bulkheads 2, 3 which may be referred to as just "device" herein). Further the electric resistance of the heaters 28 is calculated based on an electric current amount of the heaters 28. A degradation detector in this embodiment detects the degradation of the heaters 28 based on the estimated resistance of the heaters 28 and the calculated resistance of the heaters 28, which is explained below.

Figure 2:
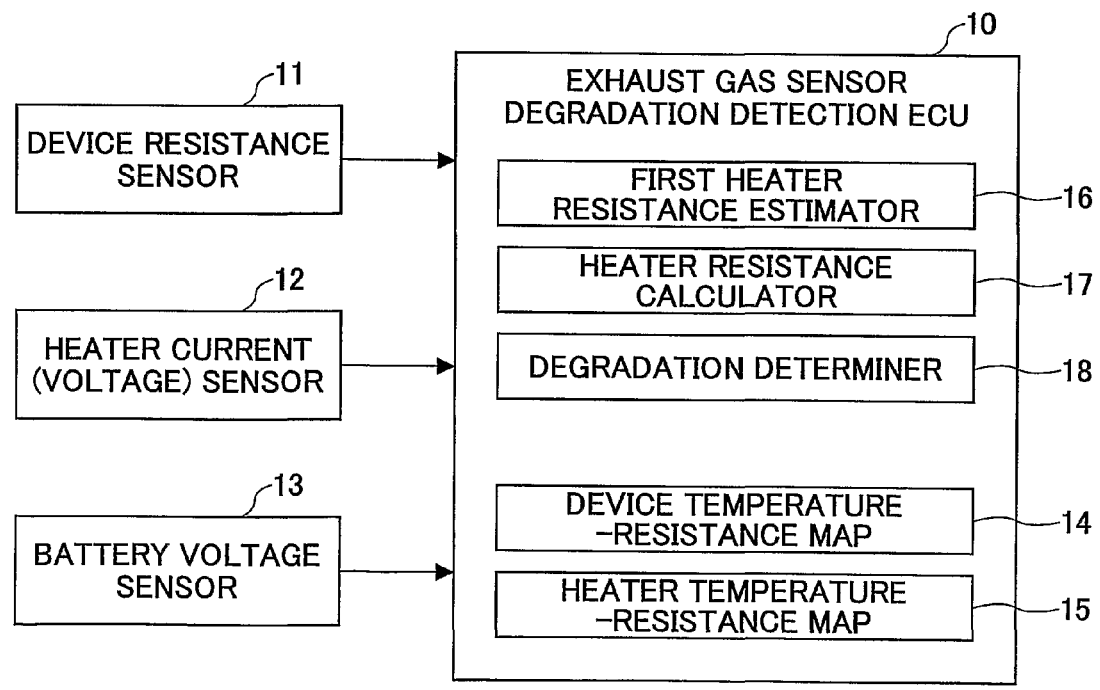
FIG. 2 is a functional block diagram of a degradation detector of the exhaust gas sensor according to a first embodiment of the present invention.

FIG. 2 is a functional block diagram of a degradation detector of the exhaust gas sensor 1 according to this embodiment of the present invention. The degradation detector of the exhaust gas sensor is controlled by an exhaust gas sensor degradation detector ECU (referred to as "degradation detector ECU" herein) 10. A device resistance sensor 11, a heater current sensor 12 and a battery voltage sensor 13 are connected to the degradation detector ECU 10. The degradation detector ECU 10 comprises a first heater resistance estimator 16, a heater resistance calculator 17, a degradation determiner 18, a device temperature-device resistance Map 14 and a heater temperature-heater resistance Map 15.

The device resistance sensor 11 detects an actual electric resistance of the solid electrolyte device based on the relationship between an applied voltage and current, and supplies a signal corresponding to the detected actual electric resistance to the degradation detector ECU 10. For example, controlling the oxygen pump electrodes 8 as a pump is temporarily stopped (for several microseconds-several milliseconds), and the device resistance sensor 11 measures a current I1 that flows when a voltage V1 is applied between the electrodes 4 and 7, and measures a current I2 that flows when a voltage V2 is applied between the electrodes 4 and 7. The device resistance sensor 11 calculates $(V1-V2)/(I1-I2)$ as a device resistance. In this manner, the actual device resistance is determined by the above calculation while the oxygen pump electrodes 8 are not controlled as a pump, and therefore it is possible to detect the actual device resistance of the device without being affected by the change in the internal resistance variation of the solid electrolyte device.

The heater current sensor 12 detects currents flowing through one or more of the heaters 28, and supplies signals corresponding to the detected current amounts to the degradation detector ECU 10.

Figure 3A:
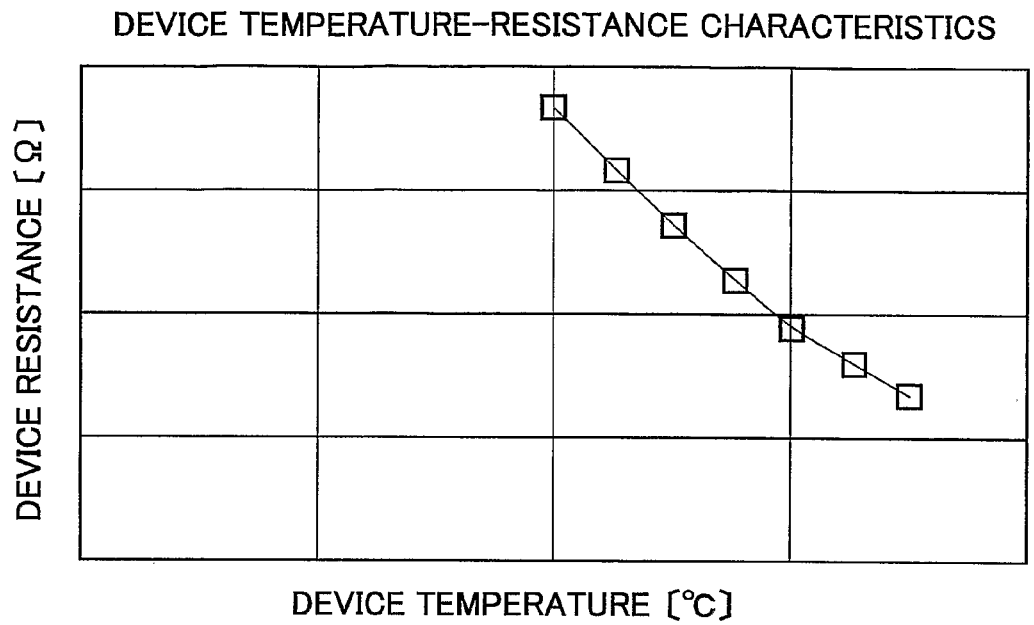
FIG. 3A is a graph showing device temperature-device resistance Map.

The device temperature-device resistance Map 14 indicates the relationship between device temperatures and device resistances as shown in FIG. 3A. If a device temperature is detected, the degradation detector ECU 10 can estimate a device resistance based on the detected device temperature by referring to the device temperature-device resistance Map 14. If a device resistance is detected, the degradation detector ECU 10 can estimate a device temperature based on the detected device resistance by referring to the device temperature-device resistance Map 14. The device temperature-device resistance Map 14 can be created by previously measuring normal device resistances corresponding to device temperatures within a predetermined device temperature range. The degradation detector ECU 10 holds the created device temperature-device resistance Map 14.

Figure 3B:
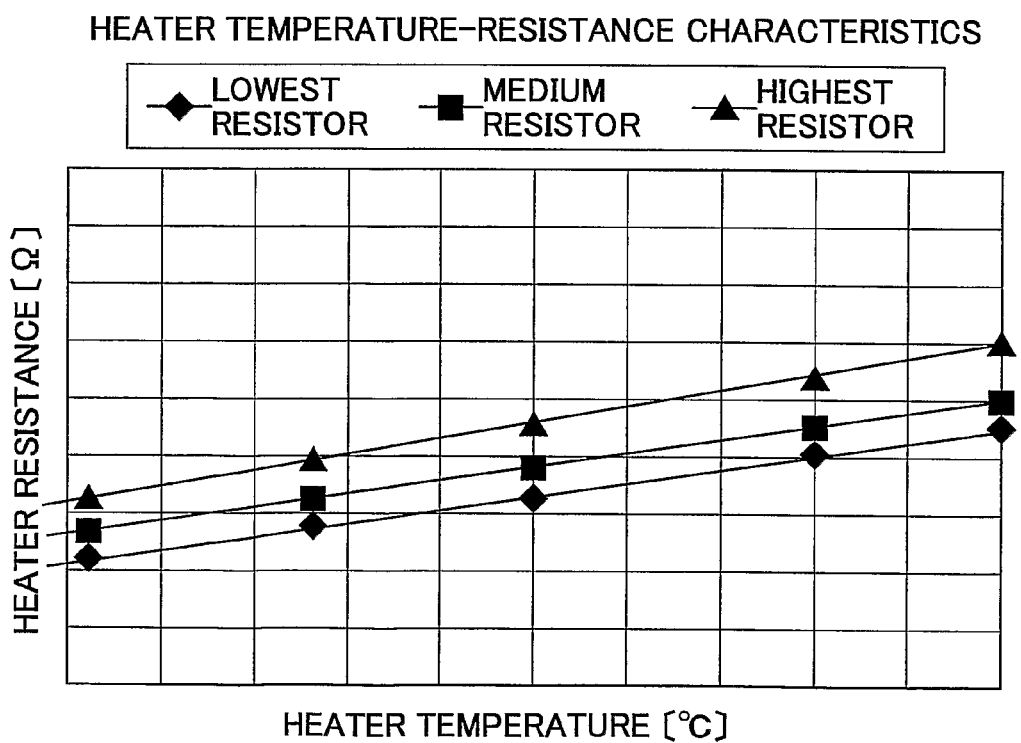
FIG. 3B is a graph showing heater temperature-heater resistance Map.

The heater temperature-heater resistance Map 15 indicates the relationship between heater temperatures and heater resistances of the normal heater 28, as shown in FIG. 3B. If a heater temperature is detected, the degradation detector ECU 10 can estimate a heater resistance based on the detected heater temperature by referring to the heater temperature-heater resistance Map 15. If a heater resistance is detected, the degradation detector ECU 10 can estimate a heater temperature based on the detected heater resistance by referring to the heater temperature-heater resistance Map 15. The heater temperature-heater resistance Map 15 can be created by previously measuring normal heater resistances corresponding to heater temperatures within a predetermined heater temperature range. The degradation detector ECU 10 holds the created heater temperature-heater resistance Map 15.

The relationships between heater temperatures and heater resistances vary from heater to heater. It is desired that the heater temperature-heater resistance Map 15 have a certain width considering the variation of each heater. FIG. 3B illustrates three relationships between heater temperatures and heater resistances. These relationships are for a lowest heater having the lowest resistances corresponding to predetermined heater temperatures, a medium heater having medium resistances, and a highest heater having the highest resistances. The heater temperature-heater resistance Map 15 is created taking the variation shown in FIG. 3b into consideration, and therefore the normal heater resistances are obtained within a range between the lowest heater and the highest heater.

The first heater resistance estimator 16 obtains a device temperature from the device temperature-device resistance Map 14, based on the detected device resistance of the exhaust gas sensor, estimates the temperature of the heaters 28 based on the obtained device temperature, and obtains a resistance of the heaters 28 from the heater temperature-heater resistance Map 15, based on the estimated heater temperature. In this manner, the first heater resistance estimator 16 can estimate the heaters 28 resistance based on the detected device resistance of the exhaust gas sensor. The heater resistance calculator 17 calculates a heater resistance, based on a current amount flowing in the heaters 28 and a voltage of the battery supplying power to the heaters 28. The degradation determiner 18 receives the estimated heater resistance from the first heater resistance estimator 16 and receives the calculated heater resistance from the heater resistance calculator 17. The degradation determiner 18 compares these two heater resistances to determine whether the exhaust gas sensor is degraded.

The operation of the exhaust gas sensor having the above structure is explained below. FIG. 4 is a flowchart illustrating a degradation detecting procedure of the exhaust gas sensor. The degradation detection of the exhaust gas sensor is performed after the heater and device temperatures become stable after an automobile engine has started.

First, the device resistance sensor 11 detects an electric resistance of the solid electrolyte device, and transmits the detected resistance value to the degradation detection ECU 10. The degradation detection ECU 10 refers to the device temperature-device resistance Map 14, and extracts or obtains a device temperature corresponding to the detected device resistance at Step S1.

The solid electrolyte devices included in the bulkheads 2, 3 are heated by the heaters 28, and therefore it is estimated that the device temperature is substantially the same as the temperature of the heaters 28. The degradation detection ECU 10 estimates a temperature of the heaters 28 based on the obtained device temperature at Step S12.

Next, the degradation detection ECU 10 refers to the heater temperature-heater resistance MAP 15, and obtains or extracts a heater resistance corresponding to the estimated heater temperature at Step S13. Since the heater temperature-heater resistance Map 15 is created based on normal heaters, the heater resistance obtained from the Map 15 should be equal to the heater resistance of normal heaters.

After obtaining the heater resistance, the degradation detection ECU 10 processes variations in individual heaters 28, and processes differences between the heater temperature and the device temperature, and a measurement error when measuring the device resistance. Based on this processing, the degradation detection ECU 10 calculates an estimated heater resistance A (that is calculated based on the device resistance) at Step S14.

The heater current sensor 12 detects an actual current amount flowing through the heaters 28, and transmits the detected current amount to the degradation detection ECU 10 at Step S15. The degradation detection ECU 10 receives a voltage of the battery supplying power to the heaters 28, from the battery voltage sensor 13. The degradation detection ECU 10 calculates an actual heater resistance B (that is calculated based on the actual heater current) at Step S16.

After calculating the estimated heater resistance A and the actual heater resistance B, the degradation detection ECU 10 determines whether the difference between the estimated heater resistance A and the actual heater resistance B is greater than a threshold at Step S17. The estimated heater resistance A is the heater resistance of normal heaters 28. The actual heater resistance B is obtained by detecting a heater current with the heater current sensor 12 and calculating predetermined equations. If the magnitude of the difference between these heater resistances is larger than the predetermined threshold, it is determined that the heaters 28 have some abnormal conditions, that is, the heaters 28 are degraded (YES at Step S17).

In a case where one of the heaters 28 is degraded in its performance, or burned out (disconnected), the calculated heater resistance B becomes larger than the normal resistance. In this case, even if the device is not well heated, the estimated heater temperature becomes lower (S12), and the obtained heater resistance is low (S13), the degradation detection ECU 10 can still detect the degradation of the heaters 28 because the heater resistance A falls within the normal range. In a case where one of the heaters 28 is degraded or disconnected, the device is heated by other normal heaters 28 and therefore the estimated heater resistance A is within the normal range. Even in this case, the degradation detection ECU 10 can still detect the degradation of the heaters 28, because the actual heater resistance B becomes larger than the heater resistance A by a predetermined threshold.

On the other hand, in a case where one of the heaters 28 is short-circuited, the calculated heater resistance B becomes lower than the normal value. In this case, irrespective of whether the device is heated or is not heated, the degradation detection ECU 10 can still detect the degradation of the heaters 28 because the estimated heater resistance A obtained based on the heater temperature falls within the normal range.

FIG. 5 is a graph showing relationships between heater temperatures and heater resistances in a case where the calculated heater resistance B is large. In FIG. 5, the heater resistance (Y axis) is plotted with respect to the device temperature (X axis). A curve a indicates the heater resistance A, and a curve b indicates the heater resistance B. A line c between the curves a and b is a threshold value for determining whether the heater is degraded or not. When the heater resistance B is larger than the line c, it is determined that the heaters 28 are degraded.

In FIG. 5, the relationships between the device temperatures and the heater resistances are shown over a certain range of device temperatures. The heater resistance B of the degraded heaters 28 is larger than the threshold value c anywhere in the whole temperature range, and therefore it is possible to detect the degradation of the heaters 28 without depending on device temperatures. The threshold value can be set lower than c as indicated by d, considering variations in individual heaters 28 as shown in FIG. 3B. If the threshold value is set as low, near to the curve, considering individual heater variations, then the degradation of the heaters 28 can be detected regardless of individual heater variations.

According to this embodiment of the present invention, even if the heater performance is degraded and its resistance is increased, the heater's resistance can be compared with the normal heater resistance, and therefore the degradation of the heater can be detected. Individual normal heater resistances have been taken into consideration and their resistance variations have been error-processed, and therefore the degradation can be detected regardless of their individual differences. The number of steps for calculating the heater resistances A and B is small and the number of newly added parts is also small, and therefore the heater degradation can be detected with reduced cost.

In FIG. 4, the degradation of the heater is detected based on the heater resistances. However, if normal relationships between heater temperature and heater currents are measured and a heater temperature-heater current MAP is previously prepared, the comparison shown in Step S17 can be performed with respect to heater currents to detect the heater degradation. Similarly, if normal relationships between heater temperature and heater voltages are measured and a heater temperature-heater voltage Map is previously prepared, the comparison shown in Step S17 can be performed with respect to heater voltages to detect the heater degradation.

Figure 6:
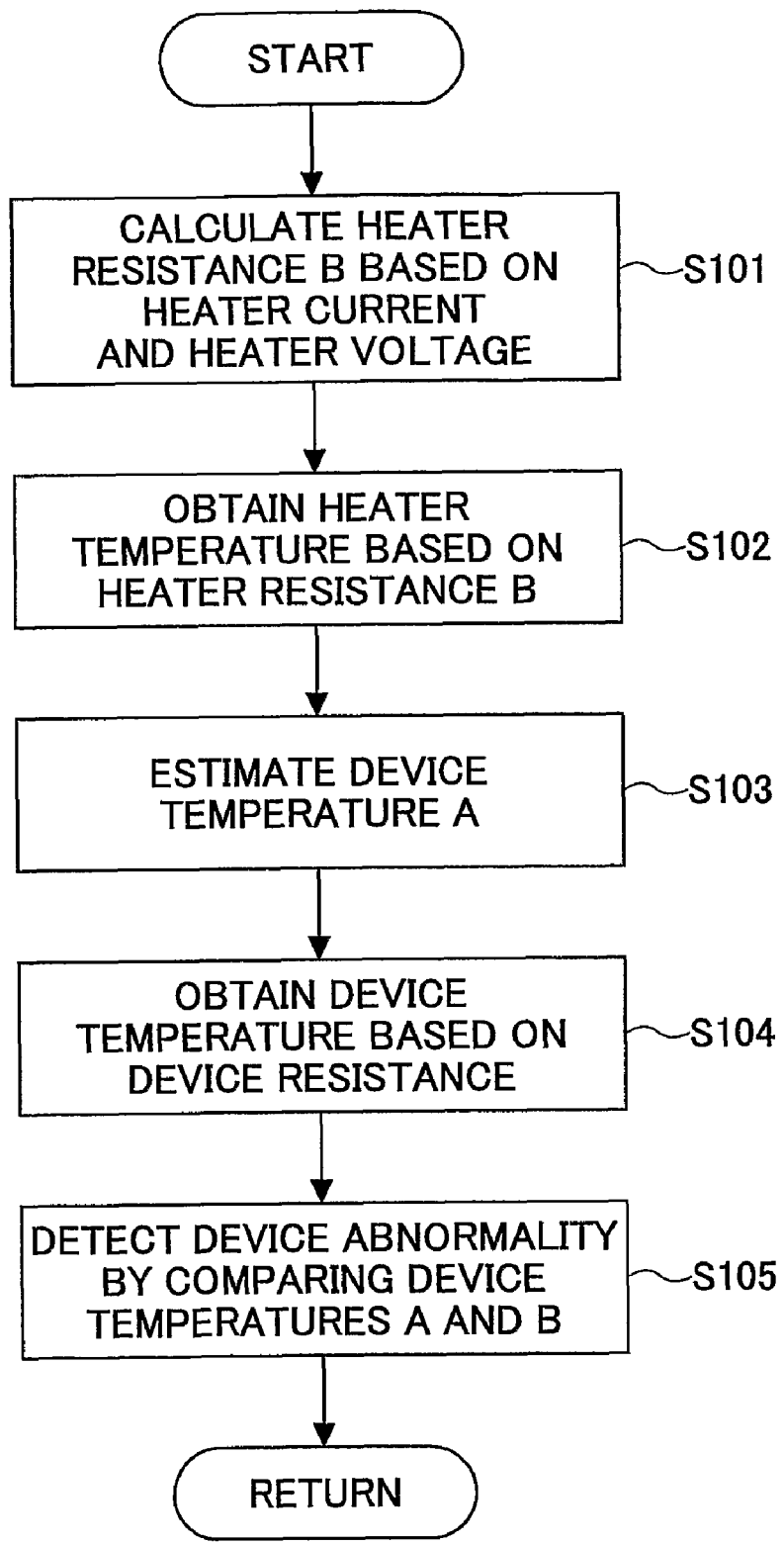
FIG. 6 is a flowchart illustrating a procedure for detecting abnormality of a solid electrolyte device based on a device temperature.

According to this embodiment of the present invention, not only the degradation of the heaters 28, but also abnormality of the solid electrolyte device can be detected. FIG. 6 is a flowchart illustrating procedure for detecting the abnormality of the solid electrolyte device based on device temperatures.

First, the degradation detection ECU 10 calculates an actual heater resistance B based on a heater current detected by the heater current sensor 12 and a battery voltage detected by the battery voltage sensor 13 at Step S101. Based on the calculated actual heater resistance B, the degradation detection ECU 10 obtains or extracts a heater temperature with reference to the heater temperature-heater resistance Map 15 shown in FIG. 3B at Step S102. Since it is believed that the obtained heater temperature is substantially the same as a device temperature, the device temperature (device temperature A) can be estimated based on the heater temperature at Step S103.

Next, based on the electric resistance of the solid electrolyte device, the degradation detection ECU 10 obtains or extracts a device temperature (device temperature B) with reference to the device temperature-device resistance Map 14 at Step S104. If the solid electrolyte device has any abnormality, it is expected that the device temperature B will be different from the device temperature A by a threshold value. Therefore, by comparing the device temperature A and the device temperature B, the degradation detection ECU 10 can detect the abnormality of the solid electrolyte device at Step S105.

Embodiment 2

Figure 7:
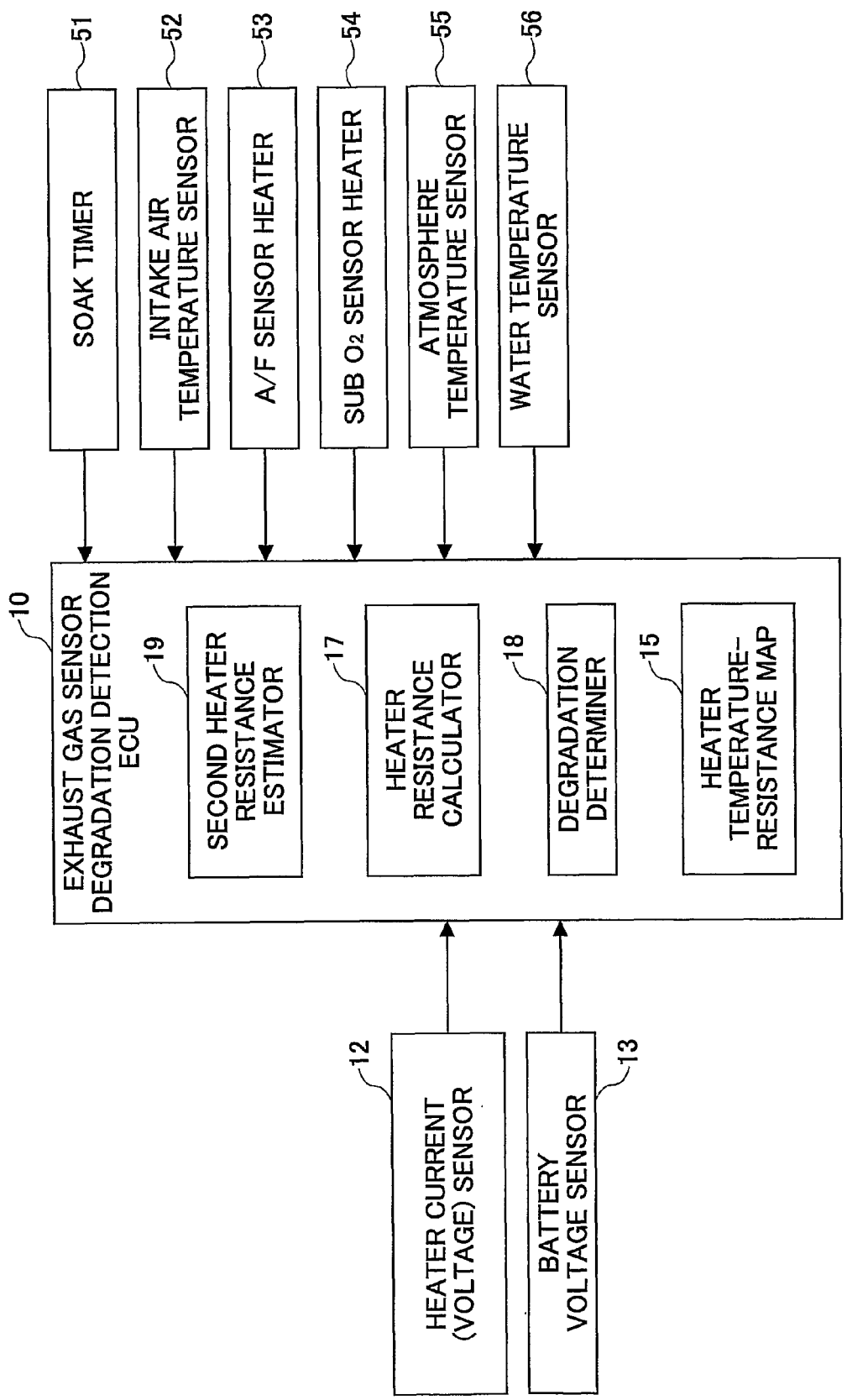
FIG. 7 is a functional block diagram of an exhaust gas sensor degradation detector according to a second embodiment of the present invention.

In this embodiment, an exhaust gas sensor degradation detector is explained, in which heater degradation is detected based on intake air or ambient temperature. FIG. 7 shows a functional block diagram of the exhaust gas sensor degradation detector according to this embodiment. In FIG. 7, the same reference numerals are assigned to parts the same as those shown in FIG. 2, and their explanation is omitted.

The exhaust gas sensor degradation detector is controlled by an exhaust gas sensor degradation detector ECU (referred to as just "degradation detector ECU" herein) 10. The degradation detector ECU 10 is connected to a soak timer 51, an intake temperature sensor 52, an A/F sensor heater, a sub $O_2$ sensor heater, an atmospheric temperature sensor 55, and a water sensor 56.

The soak timer 51 measures the elapsed time since the engine has stopped. The elapsed time is referred to as "soak time" herein, which means a time required for stabilizing components' temperatures to atmospheric temperature. The elapsed time being measured is transmitted to the degradation detection ECU 10. The intake air temperature sensor 52 detects the temperature of intake air of the engine, and transmits it to the degradation detection ECU 10. The A/F sensor heater 53 heats an A/F sensor, and detects its own temperature and transmits the temperature to the degradation detection ECU 10. The sub $O_2$ sensor heater 54 heats a sub $O_2$ sensor, and detects its own temperature and transmits the temperature to the degradation detection ECU 10. The atmospheric temperature sensor 55 and the water temperature sensor 56 detect the atmospheric temperature and engine cooling water temperature, respectively, and transmit them to the degradation detection ECU 10.

Figure 8:
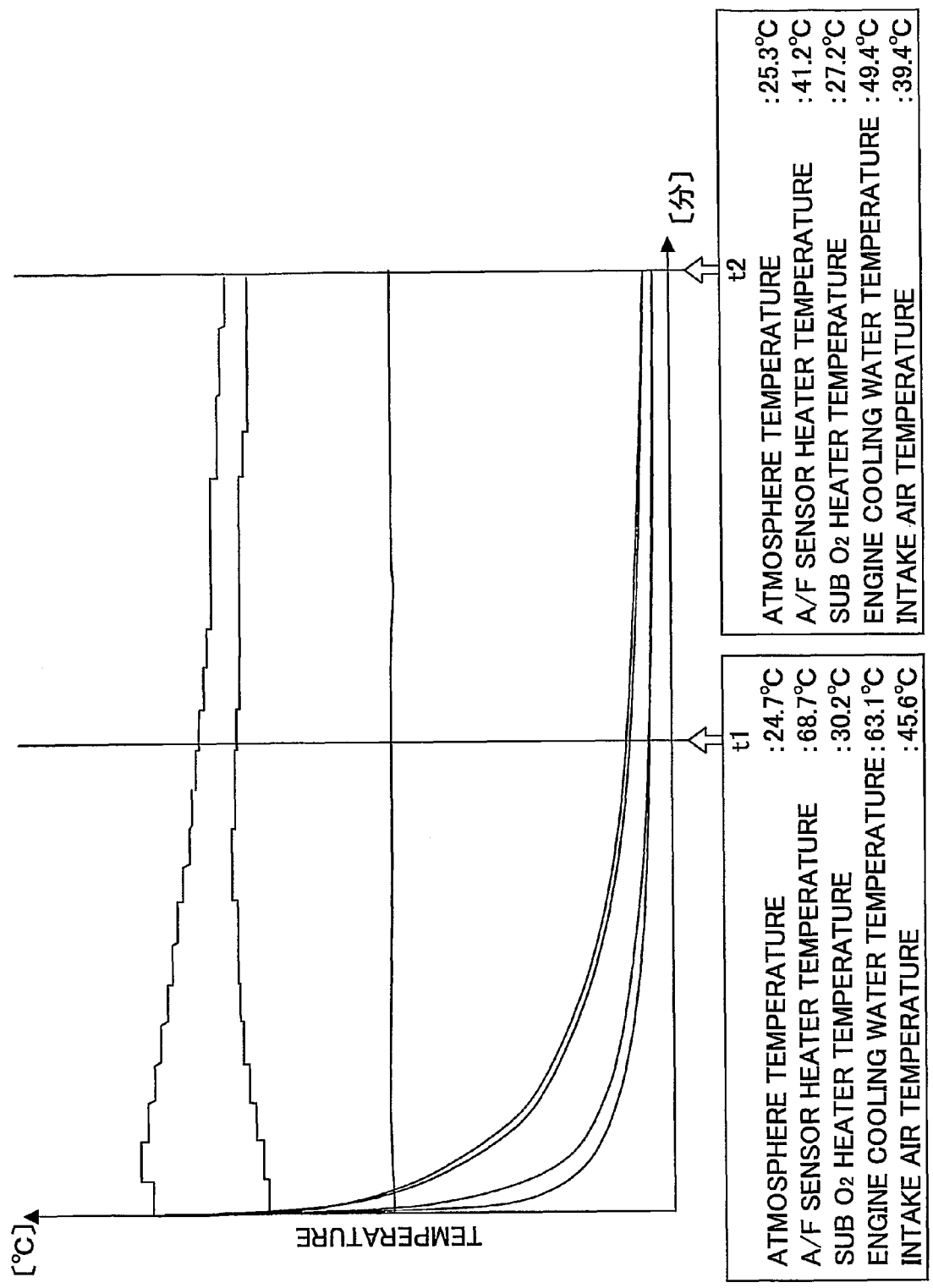
FIG. 8 is a graph showing relationships between soak time and atmospheric temperature, A/F sensor heater temperature, sub $O_2$ sensor heater temperature, engine cooling water temperature and intake air temperature.

When the engine stops, heating by the engine and power supply to the heaters are stopped. Therefore, as the time elapses after the engine is stopped, the temperatures of the heaters 28 of the exhaust gas sensor degradation detector, and the A/F sensor heater and the sub $O_2$ sensor heater 54 become gradually close to the atmospheric temperature or intake air temperature. FIG. 8 shows relationships between the soak time and the atmospheric temperature, the A/F sensor heater temperature, the sub $O_2$ sensor heater temperature, the engine cooling water temperature and the intake air temperature. The atmospheric temperature is substantially constant.

With reference to FIG. 8, when the elapsed time is t1 minutes (for example 60 minutes), the sub $O_2$ sensor heater temperature comes close to the atmospheric temperature. When the elapsed time is t2 minutes (for example 120 minutes), the A/F sensor heater temperature and the intake air temperature come closer together. Accordingly, when a certain time has passed with the engine stopped, it can be assumed that the A/F sensor heater temperature and the sub $O_2$ sensor heater temperature are substantially the same as the atmospheric temperature and the intake air temperature.

Similar to the A/F sensor heater temperature and the sub $O_2$ sensor heater temperature, it can be also assumed that the temperatures of the exhaust gas sensor detector heaters 28 become substantially the same as the atmosphere temperature and the intake air temperature when a certain time has passed since the engine had stopped. Accordingly, it is possible to estimate the atmospheric temperature, the A/F sensor heater temperature and the sub $O_2$ sensor heater temperature by using their relationships with the soak time and the A/F sensor heater, etc. If the temperature of the heaters 28 can be estimated, a heater resistance can be obtained to detect the degradation of the exhaust gas sensor, similar to embodiment 1. A second heater resistance estimator 19 estimates a resistance of the heaters 28, based on temperatures detected by temperature sensors disposed at a variety of places of the automobile.

Figure 9:
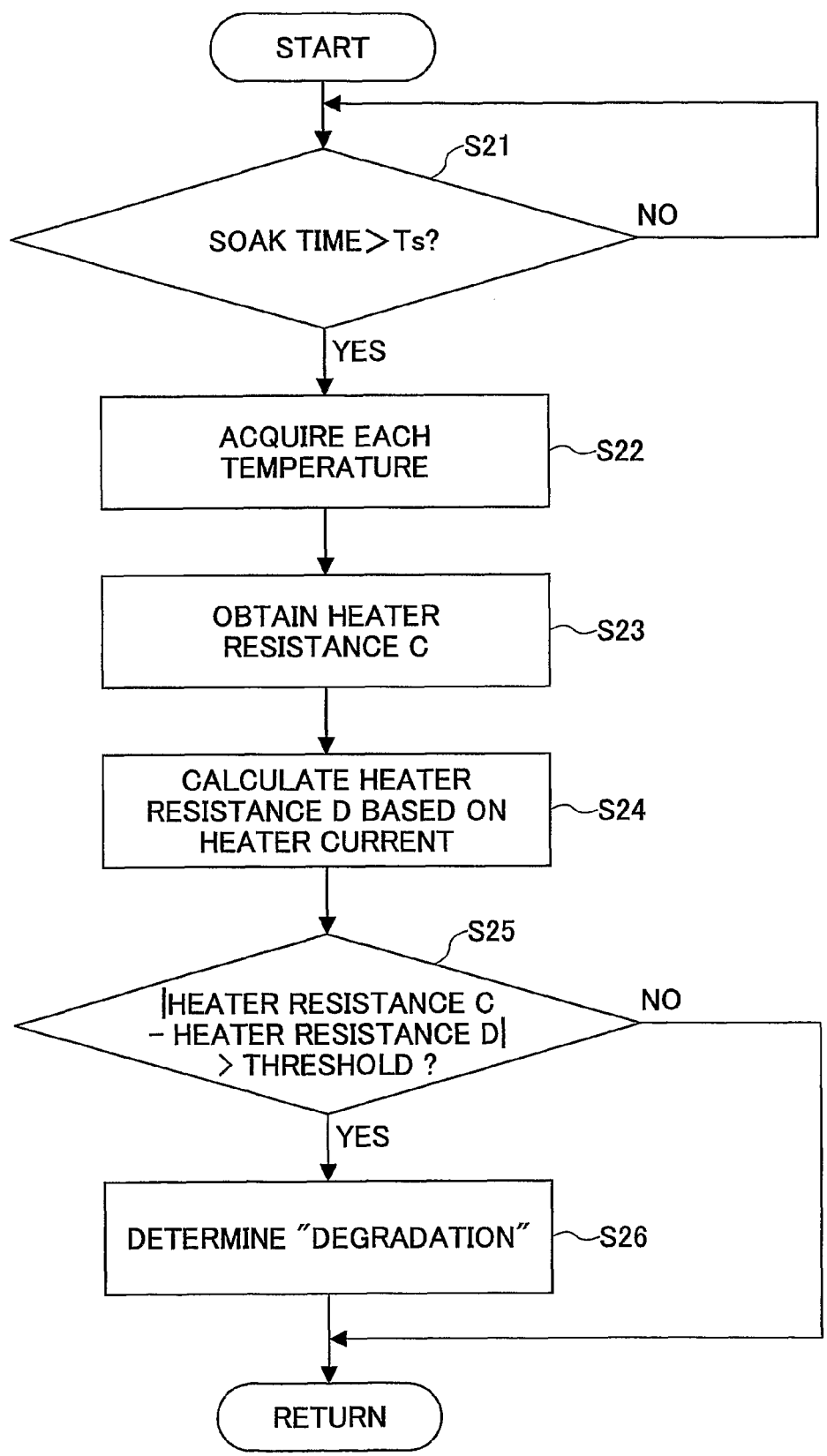
FIG. 9 is a flowchart illustrating a procedure for detecting the degradation of a heater utilizing elapsed soak time.

FIG. 9 is a flowchart illustrating a procedure for detecting the degradation of the heaters 28 after a certain soak time has passed. The procedure shown in FIG. 9 starts when the automobile engine has stopped. After the procedure shown in FIG. 9 is started, the degradation detection ECU 10 determines whether the soak time has exceeded a predetermined time Ts at Step S21. The time Ts is previously determined by measuring the relationship between the soak time and the A/F sensor heater temperature, etc., as shown in FIG. 8, in accordance with the atmospheric temperature or season. The degradation detection ECU 10 repeats its determination step S21 until the soak time becomes the time Ts.

After the soak time has exceeded the time Ts, the degradation detection ECU 10 acquires each detected temperature from the intake air temperature sensor 52, the A/F sensor heater 53, the sum $O_2$ sensor heater 54 and the atmospheric temperature sensor 55 at Step S22.

Out of the acquired temperatures, the degradation detection ECU 10 selects a temperature suitable for estimating the temperature of the heaters 28 of the exhaust gas sensor degradation detector, and assumes that the selected temperature is substantially the same as the temperature of the heaters 28. Based on the assumed heater temperature, the degradation detection ECU 10 obtains or extracts a heater resistance (the heater resistance obtained from the intake air temperature, etc., is referred to as "heater resistance C") with reference to the heater temperature-heater resistance MAP as shown in FIG. 3B.

Out of the acquired temperatures, the temperature suitable for estimating the heater temperature of the exhaust gas sensor degradation detector may be the lowest temperature, or either of the A/F sensor heater temperature or the sub $O_2$ sensor heater temperature.

Next, based on a heater current detected by the heater current sensor 12 and a battery voltage detected by the battery sensor 13, the degradation detection ECU 10 calculates a heater resistance (the heater resistance calculated based on the heater current is referred to as "heater resistance D") at Step S24.

After calculating the heater resistance C and the heater resistance D, the degradation detection ECU 10 compares them at Step S25. It can be assumed that the heater resistance C indicates a normal heater resistance because it has been obtained from the A/F sensor heater temperature of the sub O2 sensor heater temperature, etc., other than the heaters 28. The heater resistance D is the actual resistance of the heaters 28 because it has been calculated based on the value detected by the heater current sensor 12. If these heater resistances C and D are different, it is determined that the heaters 28 have been degraded at Step S26.

In a case where one of the heaters 28 is degraded in its performance, or burned out (disconnected), the calculated heater resistance D becomes larger than the normal resistance. Even in this case, the heater resistance C is substantially the same as the normal heater resistance, since it is estimated based other heater temperatures such as the A/F sensor heater, etc. Even in this case, the degradation detection ECU 10 can still detect the degradation of the heaters 28, because the heater resistance D becomes larger than the heater resistance C by a predetermined threshold.

On the other hand, in a case where one of the heaters 28 is short-circuited, the calculated heater resistance D becomes lower than the normal value. In this case, the heater resistance C has been estimated based on other temperature sensors, and therefore the heater resistance C becomes the normal value. Accordingly, the heater resistance D becomes smaller than the heater resistance C by a predetermined threshold, and the degradation detection ECU 10 can detect that the heaters 28 are degraded.

If the difference between the heater resistances C and D is within the threshold, it is determined that the heaters 28 are not degraded and the procedure ends.

According to this embodiment of the present invention, the heater resistance D can be obtained by the soak timer 51, and the degradation of the heaters 28 can be accurately detected based on the heater resistance D and the heater resistance C calculated based on the heater current. The number of steps for calculating the heater resistances C and D is small and the number of newly added parts is also small, and therefore the heater degradation can be detected with reduced cost.

As explained above, according to the embodiments of the present invention, the exhaust gas sensor degradation detector can detect the degradation of a heater based on its resistance, and can detect the degradation of the exhaust gas sensor precisely. It is possible to detect the degradation of the exhaust gas sensor not only based on the heater resistance, but also based a heater current and voltage. Further it is possible to detect the degradation of the exhaust gas sensor not only based on the heater degradation but also based on the abnormality of the solid electrolyte device.

The present application is based on Japanese Priority Application No. 2005-011572 filed on Jan. 19, 2005 with the Japanese Patent Office, the entire contents of which are hereby incorporated by reference.

The invention claimed is:

1. A degradation detecting method in a vehicle exhaust gas sensor comprising the steps of:
    estimating a resistance of a heater that heats the exhaust gas sensor, based on a plurality of temperatures detected by a plurality of temperature sensors provided at places of the vehicle;
    calculating a resistance of the heater, based on a heater current of the heater; and
    determining whether the heater is degraded and thereby determining whether the exhaust gas sensor is degraded, by comparing the estimated resistance of the heater and the calculated resistance of the heater.

2. The degradation detecting method as claimed in claim 1, further comprising the step of:
    preparing a heater temperature-heater resistance map for storing a relationship between temperatures of the heater and the heater resistances;
    wherein
    the step of estimating a resistance of a heater includes the steps of
        estimating the heater temperature when a soak time exceeded a predetermined value, based on the plurality of temperatures detected by the plurality of temperature sensors; and
        obtaining a heater temperature from the heater temperature-heater resistance map, based on the estimated heater resistance.

3. The degradation detecting method as claimed in claim 1, wherein
    the step of estimating a resistance of a heater includes a step of estimating the heater temperature, based on one or more of an intake air temperature, an A/F sensor heater temperature, a sub O2 sensor heater temperature, an atmospheric temperature or an engine cooling water temperature.

4. A degradation detector of a vehicle exhaust gas sensor comprising:
    a heater resistance estimator for estimating a resistance of a heater that heats the exhaust gas sensor, based on a plurality of temperatures detected by a plurality of temperature sensors provided at places of the vehicle;
    a heater resistance calculator for calculating a resistance of the heater, based on a heater current of the heater; and
    a degradation determiner for determining whether the heater is degraded and thereby determining whether the exhaust gas sensor is degraded, by comparing the estimated resistance of the heater and the calculated resistance of the heater.

5. The degradation detector as claimed in claim 4, further comprising:
    a heater temperature-heater resistance map for storing a relationship between temperatures of the heater and the heater resistances;
    wherein
    the heater resistance estimator estimates the heater temperature when a soak time exceeded a predetermined value, based on the plurality of temperatures detected by the plurality of temperature sensors; and
    obtains a heater temperature from the heater temperature-heater resistance map, based on the estimated heater resistance.

6. The degradation detector as claimed in claim 4, wherein the heater resistance estimator estimates the heater temperature, based on one or more of an intake air temperature, an A/F sensor heater temperature, a sub O2 sensor heater temperature, an atmospheric temperature or an engine cooling water temperature.

\* \* \* \* \*